US008900147B2

(12) United States Patent
Yoo et al.

(10) Patent No.: US 8,900,147 B2
(45) Date of Patent: Dec. 2, 2014

(54) PERFORMING IMAGE PROCESS AND SIZE MEASUREMENT UPON A THREE-DIMENSIONAL ULTRASOUND IMAGE IN AN ULTRASOUND SYSTEM

(75) Inventors: Jae Heung Yoo, Seoul (KR); Eun Ho Yang, Seoul (KR)

(73) Assignee: Samsung Medison Co., Ltd., Gangwon-do (KR)

( * ) Notice: Subject to any disclaimer, the term of this patent is extended or adjusted under 35 U.S.C. 154(b) by 379 days.

(21) Appl. No.: 13/013,306

(22) Filed: Jan. 25, 2011

(65) Prior Publication Data

US 2011/0184290 A1   Jul. 28, 2011

(30) Foreign Application Priority Data

Jan. 26, 2010   (KR) .................. 10-2010-0006722

(51) Int. Cl.
*A61B 8/00* (2006.01)
*A61B 8/08* (2006.01)
*G06T 7/00* (2006.01)
*G01S 15/89* (2006.01)

(52) U.S. Cl.
CPC .............. *A61B 8/00* (2013.01); *G01S 15/8993* (2013.01); *A61B 8/483* (2013.01); *G06T 7/0097* (2013.01); *G06T 2207/30101* (2013.01); *G06T 7/0083* (2013.01); *G06T 2207/20101* (2013.01); *G06T 2207/10136* (2013.01)
USPC ............ 600/443; 600/437; 600/407; 600/441

(58) Field of Classification Search
None
See application file for complete search history.

(56) References Cited

U.S. PATENT DOCUMENTS

| | | | |
|---|---|---|---|
| 6,290,648 B1 * | 9/2001 | Kamiyama | 600/443 |
| 6,694,163 B1 | 2/2004 | Vining | |
| 2003/0152262 A1 | 8/2003 | Mao et al. | |
| 2003/0174872 A1 * | 9/2003 | Chalana et al. | 382/128 |

(Continued)

FOREIGN PATENT DOCUMENTS

| | | |
|---|---|---|
| EP | 1 892 671 A2 | 2/2008 |
| EP | 2 098 993 A1 | 9/2009 |

(Continued)

OTHER PUBLICATIONS

Korean Office Action issued in Korean Patent Application No. KR 10-2010-0006722 dated Apr. 14, 2011.
Extended European Search Report ssued in European Patent Application No. 11151476.6 dated Jun. 7, 2011.

*Primary Examiner* — Joel Lamprecht
(74) *Attorney, Agent, or Firm* — McDermott Will & Emery LLP

(57) ABSTRACT

Embodiments for performing an image process and a size measurement upon a three-dimensional ultrasound image are disclosed. In one embodiment, by way of non-limiting example, an ultrasound system comprises: a user input unit configured to receive input information for setting at least one seed point on a two-dimensional ultrasound image from a user; an ultrasound data acquisition unit configured to transmit and receive ultrasound signals to and from a target object including a plurality of objects of interest and output ultrasound data; and a processing unit configured to form volume data based on the ultrasound data, form the two-dimensional ultrasound image and a three-dimensional ultrasound image based on volume data, detect at least one object of interest corresponding to the input information from the three-dimensional ultrasound image, and perform an image process and a size measurement of the detected object of interest upon the three-dimensional ultrasound image.

7 Claims, 10 Drawing Sheets

(56) References Cited

U.S. PATENT DOCUMENTS

| | | |
|---|---|---|
| 2007/0133852 A1 | 6/2007 | Collins et al. |
| 2008/0097209 A1 | 4/2008 | Lee et al. |
| 2008/0118118 A1 | 5/2008 | Berger |
| 2008/0234583 A1 | 9/2008 | Choi |
| 2008/0292169 A1 | 11/2008 | Wang et al. |
| 2008/0304730 A1 | 12/2008 | Abe |

FOREIGN PATENT DOCUMENTS

| | | |
|---|---|---|
| JP | 05-137728 | 6/1993 |
| JP | 2008-301920 | 12/2008 |
| KR | 10-2008-0035163 | 4/2008 |
| KR | 10-2008-0085420 | 9/2008 |

* cited by examiner

PERFORMING IMAGE PROCESS AND SIZE MEASUREMENT UPON A THREE-DIMENSIONAL ULTRASOUND IMAGE IN AN ULTRASOUND SYSTEM

CROSS-REFERENCE TO RELATED APPLICATIONS

The present application claims priority from Korean Patent Application No. 10-2010-0006722 filed on Jan. 26, 2010, the entire subject matter of which is incorporated herein by reference.

TECHNICAL FIELD

The present disclosure generally relates to ultrasound systems, and more particularly to performing an image process and size measurement upon a three-dimensional (3D) ultrasound image in an ultrasound system.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two-dimensional (2D) or three-dimensional (3D) ultrasound images of internal features of an object (e.g., human organs).

The ultrasound system may provide the 3D ultrasound image including clinical information such as spatial information and anatomical figures of the target object, which cannot be provided by the 2D ultrasound image. The ultrasound system may transmit ultrasound signals into a target object and receive ultrasound echo signals reflected from the target object. The ultrasound system may further form volume data based on the ultrasound echo signals. The ultrasound system may further render the volume data to thereby form the 3D ultrasound image.

The ultrasound system may provide the 3D ultrasound image and the 2D ultrasound image corresponding to an A plane, a B plane and a C plane, which may be mutually orthogonal. However, there is a problem in that it is difficult to estimate how the objects of interest shown in the 2D ultrasound image are three-dimensionally indicated and what sizes the objects of interest have in the 3D ultrasound image.

SUMMARY

Embodiments for providing a plurality of slice images in an ultrasound system are disclosed herein. In one embodiment, by way of non-limiting example, an ultrasound system comprises: a user input unit configured to receive input information for setting at least one seed point on a two-dimensional ultrasound image from a user; an ultrasound data acquisition unit configured to transmit and receive ultrasound signals to and from a target object including a plurality of objects of interest and output ultrasound data; and a processing unit in communication with the user input unit and the ultrasound data acquisition unit, the processing unit being configured to form volume data based on the ultrasound data, form the two-dimensional ultrasound image and a three-dimensional ultrasound image based on volume data, detect at least one object of interest corresponding to the input information from the three-dimensional ultrasound image, and perform an image process and a size measurement of the detected object of interest upon the three-dimensional ultrasound image.

In another embodiment, there is provided a method of performing an image process and a size measurement upon a three-dimensional ultrasound image, comprising: a) transmitting and receiving ultrasound signals to and from a target object including a plurality of objects of interest and output ultrasound data; b) forming volume data based on the ultrasound data; c) forming a two-dimensional ultrasound image and a three-dimensional ultrasound image based on the volume data; d) receiving input information for setting at least one seed point on the two-dimensional ultrasound image; e) detecting at least one object of interest corresponding to the input information from the three-dimensional ultrasound image; and f) performing an image process and a size measurement of the detected object of interest upon the three-dimensional ultrasound image.

In yet another embodiment, there is provided a computer readable medium comprising computer executable instructions configured to perform the following acts: a) acquiring ultrasound data for a target object including a plurality of objects of interest; b) forming volume data based on the ultrasound data; c) forming a two-dimensional ultrasound image and a three-dimensional ultrasound image based on the volume data; d) receiving input information for setting at least one seed point on the two-dimensional ultrasound image; e) detecting at least one object of interest corresponding to the input information from the three-dimensional ultrasound image; and f) performing an image process and a size measurement of the detected object of interest upon the three-dimensional ultrasound image.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
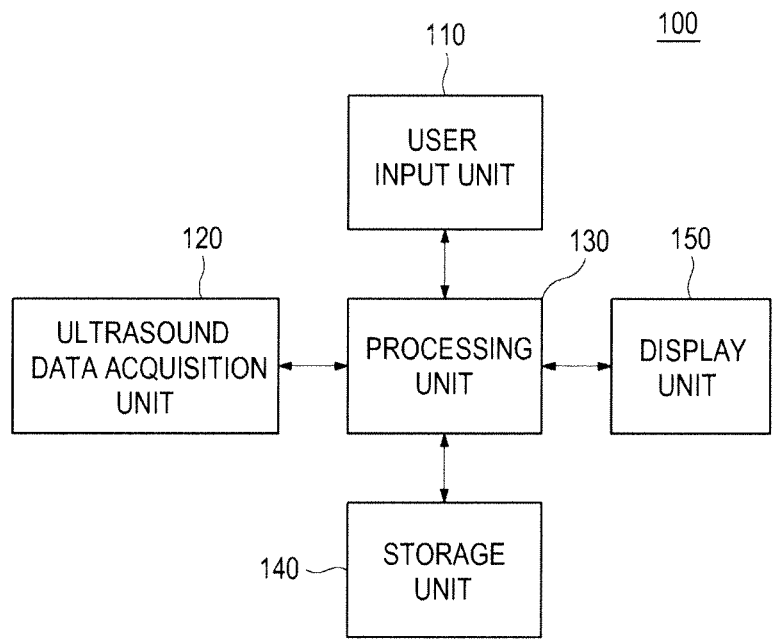
FIG. 1 is a block diagram showing an illustrative embodiment of an ultrasound system.

Referring to FIG. 1, an ultrasound system 100 in accordance with an illustrative embodiment is shown. As depicted therein, the ultrasound system 100 may include a user input unit 110. The user input unit 110 may be configured to receive input information for setting at least one seed point on a two-dimensional (2D) ultrasound image. The user input unit 110 may include a control panel, a mouse or a keyboard. However, it should be noted herein that the user input unit 110 may not be limited thereto.

The ultrasound system 100 may further include an ultrasound data acquisition unit 120. The ultrasound data acquisition unit 120 may be configured to transmit and receive ultrasound signals to and from a target object and output ultrasound data. The target object may include a plurality of objects of interest (e.g., blood vessels, a heart, etc.).

Figure 2:
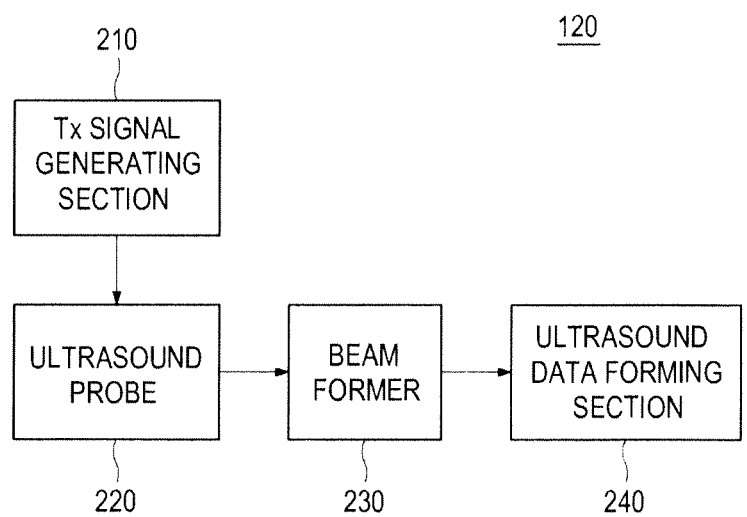
FIG. 2 is a block diagram showing an illustrative embodiment of an ultrasound data acquisition unit.

FIG. 2 is a block diagram showing an illustrative embodiment of the ultrasound data acquisition unit 120. Referring to FIG. 2, the ultrasound data acquisition unit 120 may include a transmit (Tx) signal generating section 210, an ultrasound probe 220, a beam former 230 and an ultrasound data forming section 240.

The Tx signal generating section 210 may be configured to generate Tx signals. In one embodiment, the Tx signal generating section 210 may generate Tx signals for obtaining a plurality of frames $F_i$ $(1 \leq i \leq N)$ corresponding to a three-dimensional (3D) ultrasound image at every predetermined time, as shown in FIG. 3.

Figure 3:
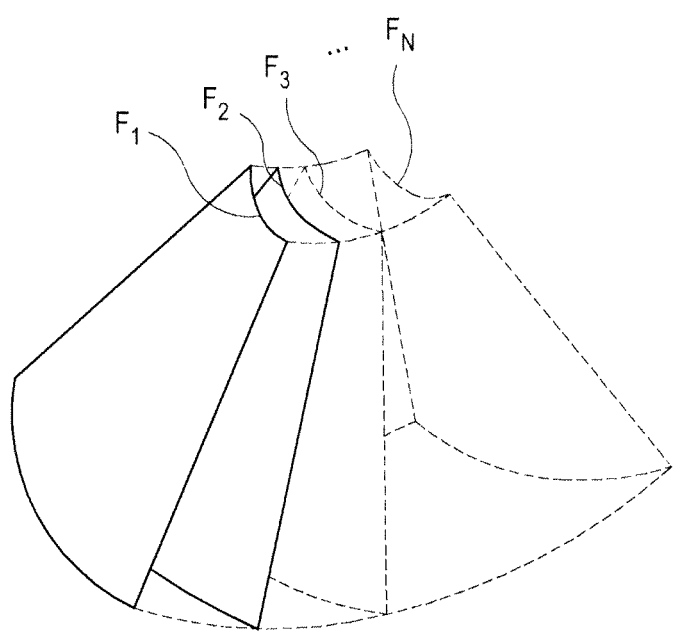
FIG. 3 is a schematic diagram showing an example of acquiring ultrasound data corresponding to a plurality of frames.

FIG. 3 is a schematic diagram showing an example of acquiring ultrasound data corresponding to the plurality of frames $F_i$ $(1 \leq i \leq N)$. The plurality of frames $F_i$ $(1 \leq i \leq N)$ may represent sectional planes of the target object (not shown).

Referring back to FIG. 2, the ultrasound probe 220 may include a plurality of elements (not shown) for reciprocally converting between ultrasound signals and electrical signals. The ultrasound probe 220 may be configured to transmit ultrasound signals to the target object in response to the Tx signals provided from the Tx signal generating section 210. The ultrasound probe 220 may further receive ultrasound signals (i.e., ultrasound echo signals) from the target object and output the received signals. The received signals may be analog signals. The ultrasound probe 220 may include a three-dimensional (3D) mechanical probe or a two-dimensional (2D) array probe. However, it should be noted herein that the ultrasound probe 220 may not be limited thereto.

The beam former 230 may be configured to convert the received signals provided from the ultrasound probe 220 into digital signals. The beam former 230 may further apply delays to the digital signals in consideration of the elements and focal points to output digital receive-focused signals.

The ultrasound data forming section 240 may be configured to form ultrasound data corresponding to the frames $F_i$ $(1 \leq i \leq N)$ based on the digital receive-focused signals provided from the beam former 230. The ultrasound data forming section 240 may further perform various signal processing (e.g., gain adjustment) upon the digital receive-focused signals.

Referring back to FIG. 1, the ultrasound system 100 may further include a processing unit 130 in communication with the user input unit 110 and the ultrasound data acquisition unit 120. The processing unit 130 may include a central processing unit, a microprocessor or a graphic processing unit. However, it should be noted herein that the processing unit 130 may not be limited thereto.

Figure 4:
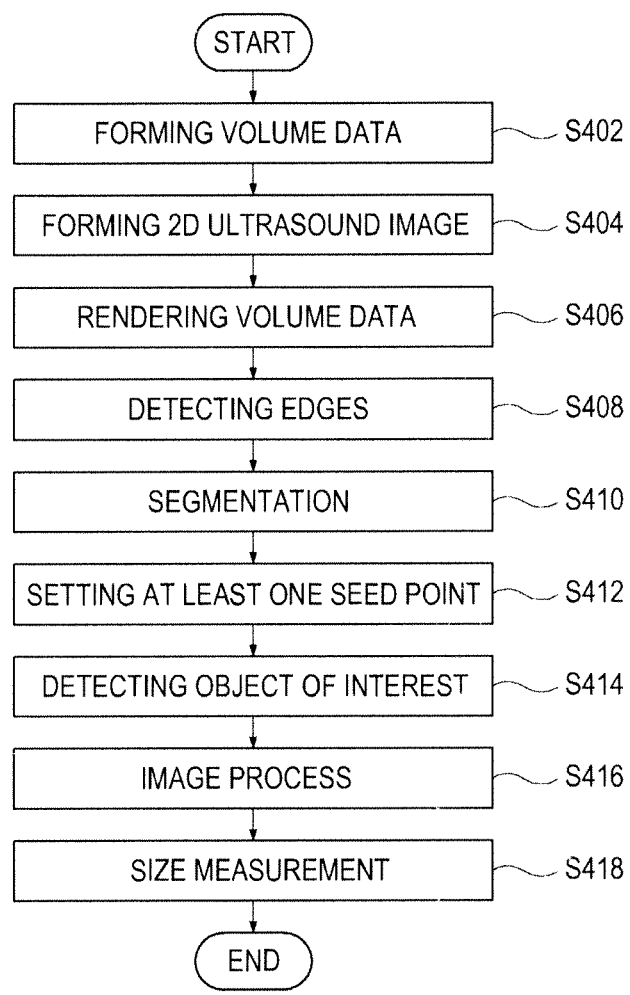
FIG. 4 is a flow chart showing a process of performing an image process and a size measurement upon a three-dimensional (3D) ultrasound image.

FIG. 4 is a flow chart showing a process of performing an image process and a size measurement upon the 3D ultrasound image. The processing unit 130 may be configured to synthesize the ultrasound data corresponding to the plurality of frames $F_i$ $(1 \leq i \leq N)$ to form volume data 510 as shown in FIG. 5, at step S402 in FIG. 4.

Figure 5:
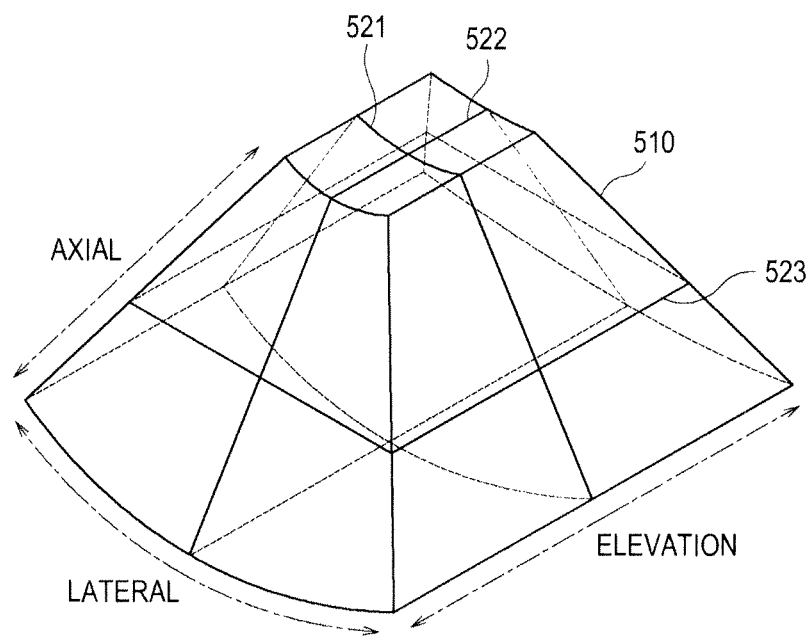
FIG. 5 is a schematic diagram showing an example of volume data.

FIG. 5 is a schematic diagram showing an example of the volume data 510. The volume data 510 may include a plurality of voxels (not shown) having brightness values. In FIG. 5, reference numerals 521, 522 and 523 represent an A plane, a B plane and a C plane, respectively. The A plane 521, the B plane 522 and the C plane 523 may be mutually orthogonal. Also, in FIG. 5, the axial direction may be a Tx direction of the ultrasound signals, the lateral direction may be a longitudinal direction of the elements, and the elevation direction may be a swing direction of the elements, i.e., a depth direction of the 3D ultrasound image.

The processing unit 130 may be configured to form the 2D ultrasound image based on the volume data 510, at step S404 in FIG. 4. The 2D ultrasound image may be displayed on a display unit 150 in FIG. 1. Thus, the user may set the at least one seed point on the 2D ultrasound image displayed on the display unit 150 by using the user input unit 110. In one embodiment, the 2D ultrasound image may be an ultrasound image corresponding to the A plane 521, the B plane 522 or the C plane 523. However, it should be noted herein that the 2D ultrasound image may not be limited thereto.

The processing unit 130 may be configured to render the volume data 510 to form the 3D ultrasound image, at step S406 in FIG. 4. The methods of rendering the volume data 510 are well known in the art. Thus, they have not been described in detail so as not to unnecessarily obscure the present invention.

The processing unit 130 may be configured to perform an edge detection of the objects of interest upon the 3D ultrasound image, at step S408 in FIG. 4. In one embodiment, the processing unit 130 may perform the edge detection by using an edge mask such as Sobel, Prewitt, Robert, Canny and the like. In another embodiment, the processing unit 130 may perform the edge detection based on a difference of eigenvalues using a structure tensor.

The processing unit 130 may be configured to perform segmentation of the objects of interest upon the 3D ultrasound image based on the detected edges, at step S410 in FIG. 5. Optionally, the processing unit 130 may further set indexes on the segmented objects of interest. The index may include a text, a figure, etc.

Figure 6:
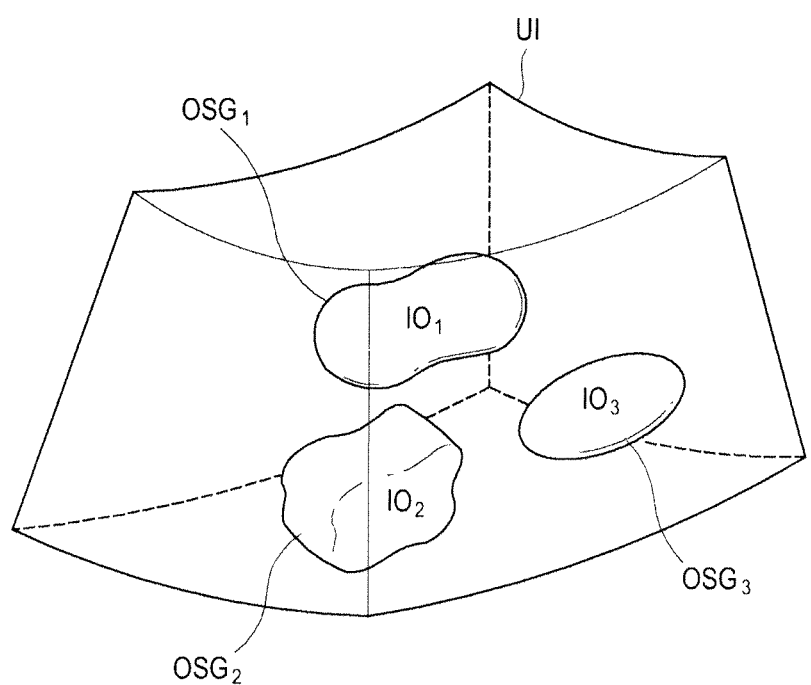
FIG. 6 is a schematic diagram showing an example of the 3D ultrasound image, a plurality of objects of interest and indexes.

In one embodiment, the processing unit 130 may perform the segmentation of the objects of interest $IO_1$, $IO_2$ and $IO_3$ upon the 3D ultrasound image UI based on the detected edges, as shown in FIG. 6. The processing unit 130 may further set indexes $OSG_1$, $OSG_2$ and $OSG_3$ on the segmented objects of interest $IO_1$, $IO_2$ and $IO_3$.

Figure 7:
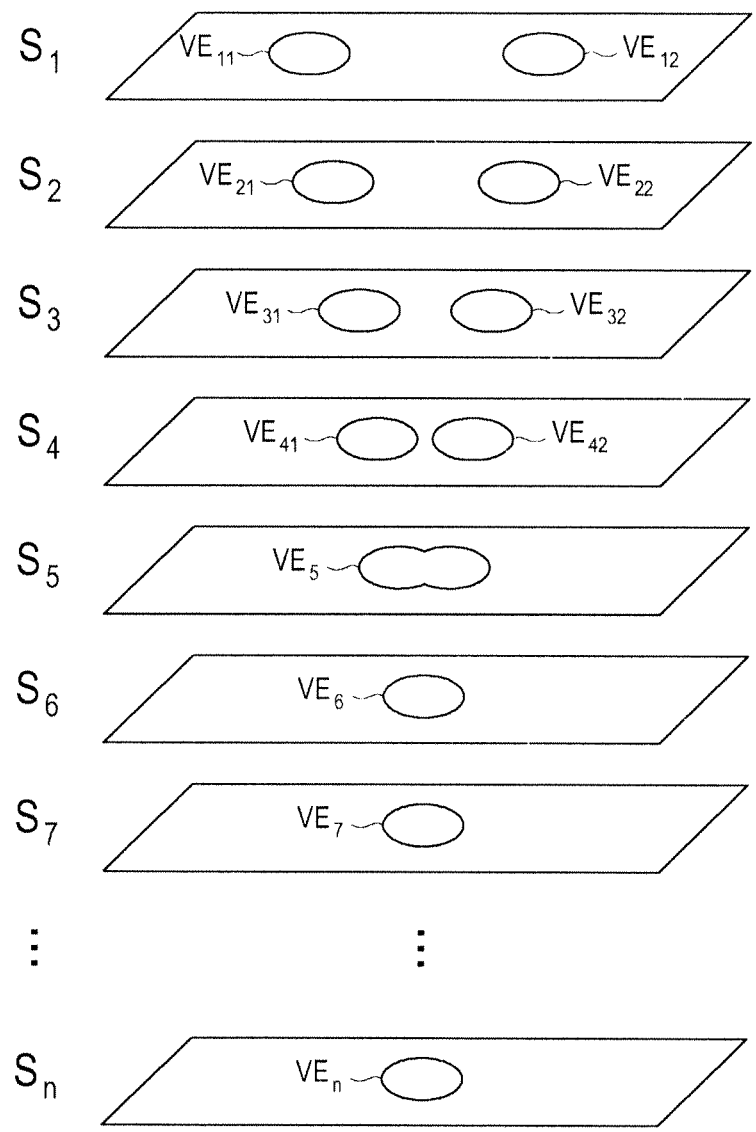
FIG. 7 is a schematic diagram showing an example of a plurality of slices and an object of interest (blood vessel).
Figure 8:
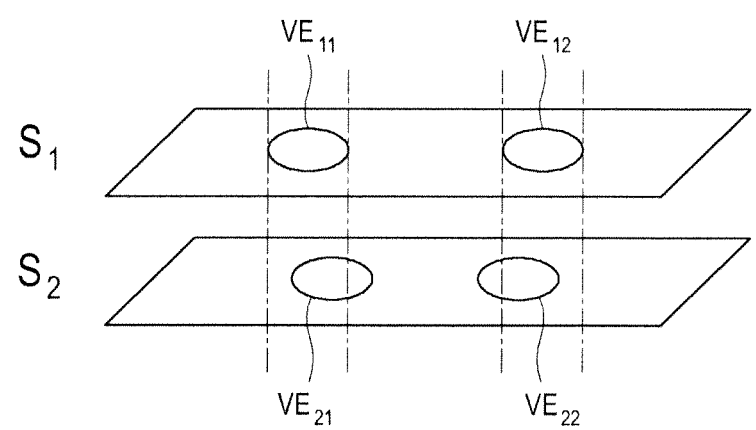
FIG. 8 is a schematic diagram showing an example of location difference between edges of the object of interest (blood vessel) on adjacent slices.
Figure 9:
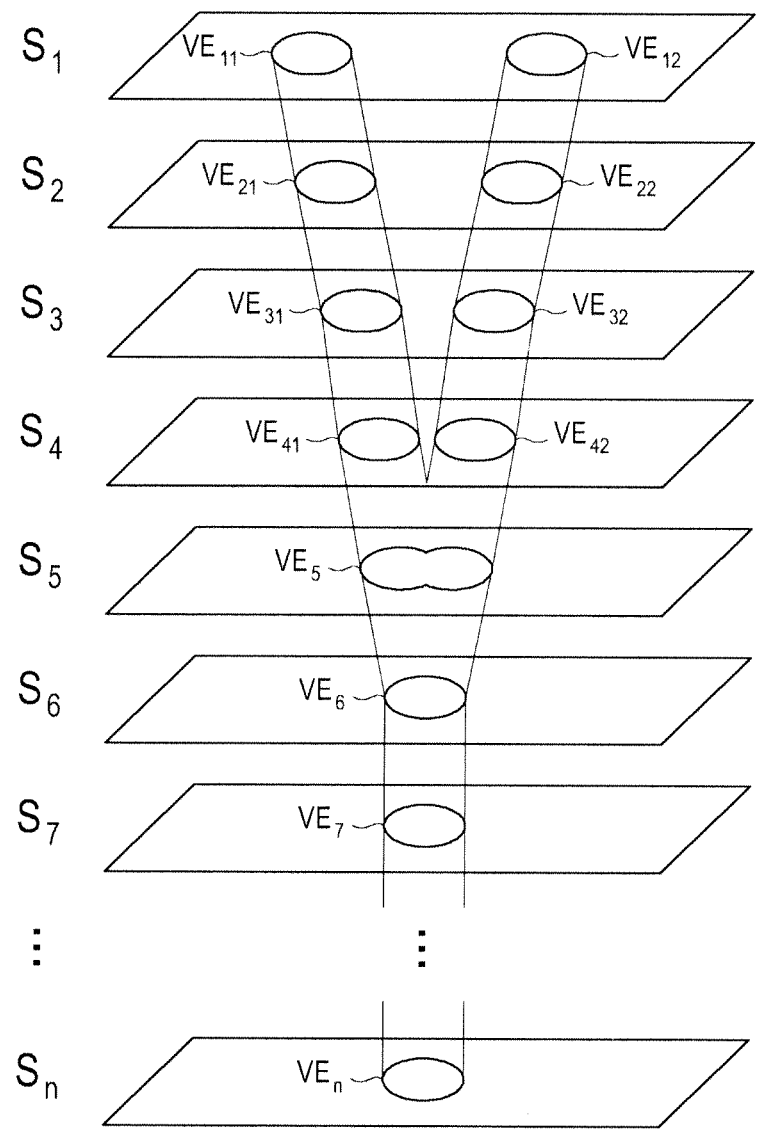
FIG. 9 is a schematic diagram showing an example of performing a segmentation of the object of interest (blood vessel).
Figure 10:
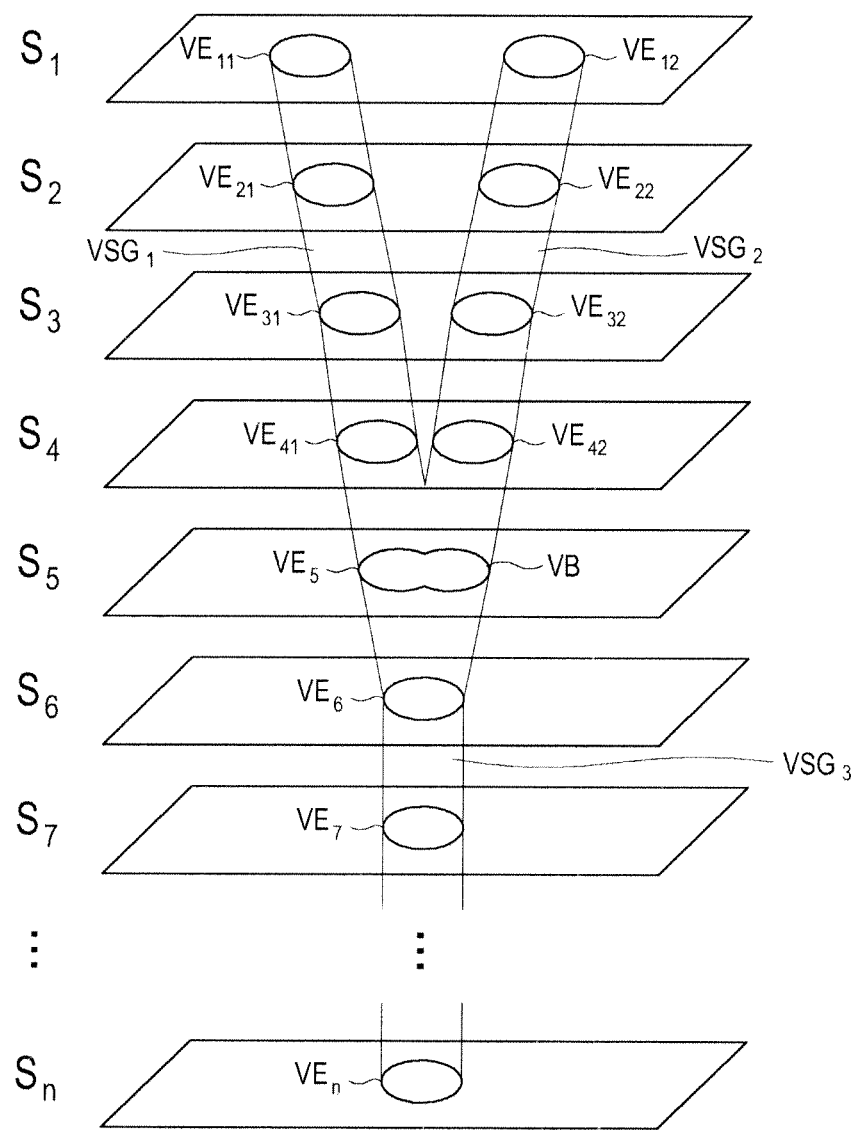
FIG. 10 is a schematic diagram showing an example of the object of interest (blood vessel) and indexes.

In another embodiment, the processing unit 130 may set a plurality of slices $S_1$ to $S_n$ on the 3D ultrasound image, as shown in FIG. 7. The slices may correspond to the frames $F_i$ $(1 \leq i \leq N)$. However, it should be noted herein that the slices may not be limited thereto. The processing unit 130 may further analyze a first slice $S_1$ to detect edges $VE_{11}$, $VE_{12}$ of the object of interest (i.e., a blood vessel) from the first slice $S_1$. The processing unit 130 may further analyze a second slice $S_2$ to detect edges $VE_{21}$, $VE_{22}$ of the object of interest from the second slice $S_2$. The processing unit 130 may further compare the edge $VE_{21}$ of the second slice $S_2$ with the edge $VE_{11}$ of the first slice $S_1$ to calculate location difference between the edges $VE_{21}$ and $VE_{11}$, as shown in FIG. 8. The processing unit 130 may further compare the edge $VE_{22}$ of the second slice $S_2$ with the edge $VE_{12}$ of the first slice $S_1$ to calculate location difference between the edges $VE_{22}$ and $VE_{12}$, as shown in FIG. 8. The processing unit 130 may further compare the edge $VE_{22}$ of the second slice $S_2$ with the edge $VE_{11}$ of the first slice $S_1$ to calculate location difference between the edges $VE_{22}$ and $VE_{11}$, as shown in FIG. 8. The processing unit 130 may further compare the edge $VE_{21}$ of the second slice $S_2$ with the edge $VE_{12}$ of the first slice $S_1$ to calculate location difference between the edges $VE_{21}$ and $VE_{12}$, as shown in FIG. 8. The processing unit 130 may further compare each of the calculated location differences with a predetermined threshold value. If it is determined that the location difference between the edges $VE_{21}$ and $VE_{11}$ and the location difference between the edges $VE_{22}$ and $VE_{12}$ are equal to or less than the threshold value, and the location difference between the edges $VE_{22}$ and $VE_{11}$ and the location difference between the edges $VE_{21}$ and $VE_{12}$ are more than the threshold value, then the processing unit 130 may further connect the edge $VE_{21}$ to the edge $VE_{11}$, and connect the edge $VE_{22}$ to the edge $VE_{12}$, as shown in FIG. 9. The processing unit 130 may perform the segmentation upon a third slice $S_3$ and a fourth slice $S_4$ as mentioned above. The processing unit 130 may further analyze a fifth slice $S_5$ to detect an edge $VE_5$ from the fifth slice $S_5$. The processing unit 130 may further compare the edge $VE_5$ of the fifth slice $S_5$ with an edge $VE_{41}$ of the fourth slice $S_4$ to calculate location difference between the edges $VE_5$ and $VE_{41}$. The processing unit 130 may further compare the edge $VE_5$ with an edge $VE_{42}$ of the fourth slice $S_4$ to calculate location difference between the edges $VE_5$ and $VE_{42}$. The processing unit 130 may further compare the calculated location differences with the threshold value. If it is determined that the location difference between the edges $VE_5$ and $VE_{41}$ and the location difference between the edges $VE_5$ and $VE_{42}$ are equal to or less than the threshold value, then the processing unit 130 may further connect the edge $VE_5$ to the edges $VE_{41}$ and $VE_{42}$. The processing unit 130 may further analyze a sixth slice $S_6$ to detect edge $VE_6$ from the sixth slice $S_6$. The processing unit 130 may further compare the edge $VE_6$ of the fifth slice $S_6$ with the edge $VE_5$ of the fifth slice $S_5$ to calculate location difference between the edges $VE_6$ and $VE_5$. The processing unit 130 may further compare the calculated location difference with the threshold value. If it is determined that the location difference between the edges $VE_6$ and $VE_5$ is equal to or less than the threshold value, then the processing unit 130 may further connect the edge $VE_6$ to the edge $VE_5$. The processing unit 130 may further perform the segmentation of the object of interest upon a seventh slice $S_7$ to an $n^{th}$ slice $S_n$ as mentioned above. The processing unit 130 may further analyze the plurality of slices $S_1$ to $S_n$ to detect a vascular bifurcation VB of the object of interest as shown in FIG. 10. The processing unit 130 may further set indexes $VSG_1$, $VSG_2$ and $VSG_3$ on the segmented object of interest based on the vascular bifurcation VB.

The processing unit 130 may be configured to set the at least one seed point corresponding to the input information on the 3D ultrasound image, at step S412 in FIG. 4. In one embodiment, the processing unit 130 may set the at least one seed point based on geometrical information of the 2D ultrasound image for the 3D ultrasound image.

The processing unit 130 may be configured to detect at least one object of interest corresponding to the at least one seed point set on the 3D ultrasound image, at step S414 in FIG. 4.

Figure 11:
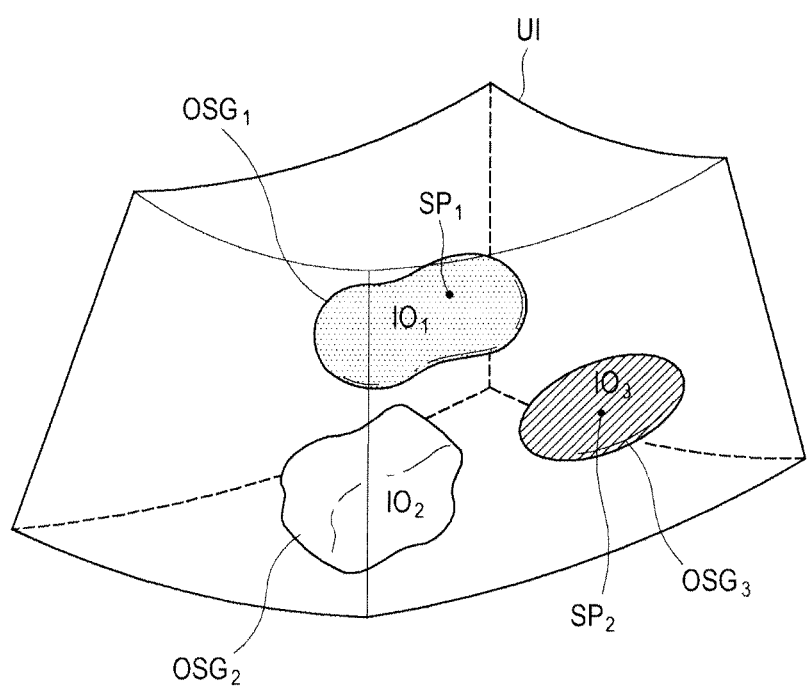
FIG. 11 is a schematic diagram showing an example of performing the image process upon the 3D ultrasound image.

The processing unit 130 may be configured to perform the image process of the detected object of upon the 3D ultrasound image, at step S416 in FIG. 4. In one embodiment, the processing unit 130 may perform the image process for applying different colors to the detected object of interest upon the 3D ultrasound image. For example, the processing unit 130 may perform the image process for applying different colors to the detected objects of interest $IO_1$ and $IO_3$ corresponding to seed points $SP_1$ and $SP_2$, respectively, upon the 3D ultrasound image UI, as shown in FIG. 11.

The processing unit 130 may be configured to perform the size measurement of the detected object of interest upon the 3D ultrasound image to form measurement information, at step S418 in FIG. 4. The methods of the size measurement are well known in the art. Thus, they have not been described in detail so as not to unnecessarily obscure the present invention.

Referring back to FIG. 1, the ultrasound system 100 may further include a storage unit 140. The storage unit 140 may store the ultrasound data acquired by the ultrasound data acquisition unit 120. The storage unit 140 may further store the volume data 510 formed by the processing unit 130.

The ultrasound system 100 may further include the display unit 150. The display unit 150 may display the 2D ultrasound image and the 3D ultrasound image formed by the processing unit 130. The display unit 150 may further display the measurement information formed by the processing unit 130.

In another embodiment, the present invention may provide a computer readable medium comprising computer executable instructions configured to perform the following acts: a) acquiring ultrasound data for a target object including a plurality of objects of interest; b) forming volume data based on the ultrasound data; c) form a two-dimensional ultrasound image and a three-dimensional ultrasound image based on the volume data; d) receiving input information for setting at least one seed point on the two-dimensional ultrasound image; e) detecting at least one object of interest corresponding to the input information from the three-dimensional ultrasound image; and f) performing an image process and a size measurement of the detected object of interest upon the three-dimensional ultrasound image. The computer readable medium may comprise a floppy disk, a hard disk, a memory, a compact disk, a digital video disk, etc.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
   a user input receiver configured to receive input information for setting at least one seed point on a two-dimensional ultrasound image from a user;
   an ultrasound data acquirer configured to transmit and receive ultrasound signals to and from a target object including a plurality of objects of interest and output ultrasound data; and a processor in communication with the ultrasound data acquirer, the processor being configured to form volume data based on the ultrasound data, form the two-dimensional ultrasound image and a three-dimensional ultrasound image based on volume data, set the at least one seed point on the two-dimensional ultrasound image based on the input information, detect at least one object of interest corresponding to the at least one seed point set on the two-dimensional ultrasound image from the three-dimensional ultrasound image, and perform an image process and a size measurement of the detected object of interest upon the three-dimensional ultrasound image, wherein the detection of the at least one object of interest is performed by connecting a first edge of the at least one object of interest corresponding to a first slice to a second edge of the at least one object of interest corresponding to a second slice, based on a result of comparison between a predetermined threshold value and a location difference between the first edge and the second edge, wherein the first slice and the second slice are slices that are set on the three-dimensional ultrasound image.

2. The ultrasound system of claim 1, wherein the processor is configured to:

perform an edge detection of the at least one object of interest upon the three-dimensional ultrasound image; and perform a segmentation of the at least one object of interest upon the three-dimensional ultrasound image based on the detected edges.

3. The ultrasound system of claim 1, wherein the processor is configured to perform the image process for applying different colors to the detected object of interest upon the three-dimensional ultrasound image.

4. A method of performing an image process and a size measurement upon a three-dimensional ultrasound image, comprising:

a) transmitting and receiving ultrasound signals to and from a target object including a plurality of objects of interest and output ultrasound data;

b) forming volume data based on the ultrasound data;

c) forming a two-dimensional ultrasound image and a three-dimensional ultrasound image based on the volume data;

d) receiving input information for setting at least one seed point on the two-dimensional ultrasound image;

e) setting the at least one seed point on the two-dimensional ultrasound image based on the input information;

f) detecting at least one object of interest corresponding to the at least one seed point set on the two-dimensional ultrasound image from the three-dimensional ultrasound image; and g) performing an image process and a size measurement of the detected object of interest upon the three-dimensional ultrasound image, wherein the step f) is performed by connecting a first edge of the at least one object of interest corresponding to a first slice to a second edge of the at least one object of interest corresponding to a second slice, based on a comparison between a predetermined threshold value and a location difference between the first edge and the second edge, wherein the first slice and the second slice are slices that are set on the three-dimensional ultrasound image.

5. The method of claim 4, wherein the step f) comprises:

performing edge detection of the at least one object of interest upon the three-dimensional ultrasound image; and performing segmentation of the at least one object of interest upon the three-dimensional ultrasound image based on the detected edges.

6. The method of claim 4, wherein the step g) comprises:

performing the image process for applying different colors to the detected object of interest upon the three-dimensional ultrasound image.

7. A non-transitory computer readable medium comprising computer executable instructions, execution of which causes a processor to perform following acts:

a) acquiring ultrasound data for a target object including a plurality of objects of interest;

b) forming volume data based on the ultrasound data;

c) forming a two-dimensional ultrasound image and a three-dimensional ultrasound image based on the volume data;

d) receiving input information for setting at least one seed point on the two-dimensional ultrasound image;

e) setting the at east one seed point on the two-dimensional ultrasound image based on the input information;

f) detecting at least one object of interest corresponding to the at least one seed point set on the two-dimensional ultrasound image from the three-dimensional ultrasound image; and g) performing an image process and a size measurement of the detected object of interest upon the three-dimensional ultrasound image, wherein the step f) is performed by connecting a first edge of the at least one object of interest corresponding to a first slice to a second edge of the at least one object of interest corresponding to a second slice, based on a comparison between a predetermined threshold value and a location difference between the first edge and the second edge, wherein the first slice and the second slice are slices that are set on the three-dimensional ultrasound image.

* * * * *